Figure 1:
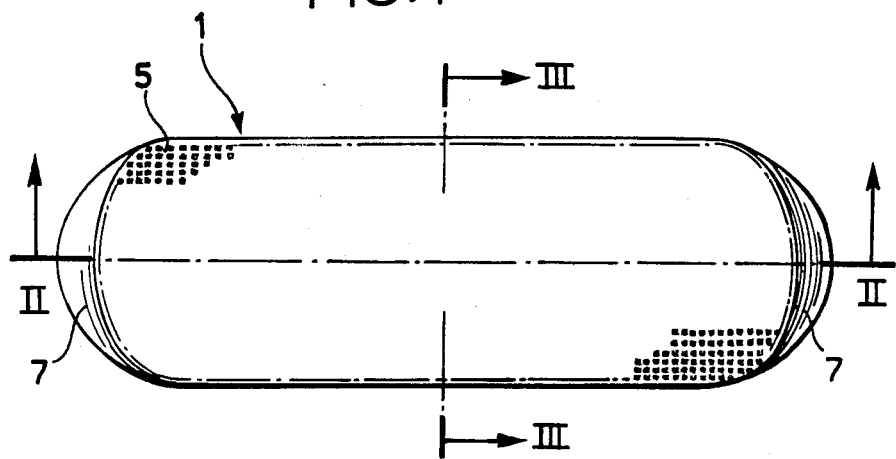

United States Patent [19]

Palumbo

[11] Patent Number: 4,780,352
[45] Date of Patent: Oct. 25, 1988

[54] COVERING STRUCTURE FOR ABSORBENT HYGIENIC-SANITARY PRODUCTS, AND AN ABSORBENT PRODUCT HAVING SUCH A COVERING

[75] Inventor: Gianfranco Palumbo, Pescara, Italy

[73] Assignee: Faricerca S.p.A., Pescara, Italy

[21] Appl. No.: 881,981

[22] Filed: Jul. 3, 1986

[30] Foreign Application Priority Data

Jul. 4, 1985 [IT]  Italy ................................ 67619 A/85

[51] Int. Cl.[4] ........................ B32B 3/10; A41B 13/02; A61F 13/18
[52] U.S. Cl. ..................................... 428/138; 428/175; 428/219; 428/303; 604/367; 604/372; 604/378
[58] Field of Search ............... 428/138, 141, 175, 219, 428/300, 332; 604/367, 372, 374, 378, 379, 383

[56] References Cited

U.S. PATENT DOCUMENTS

| | | |
|---|---|---|
| 3,929,135 | 12/1975 | Thompson . |
| 3,965,906 | 6/1976 | Karami ................................ 604/383 |
| 4,055,180 | 10/1977 | Karami ................................ 604/374 |
| 4,173,046 | 11/1979 | Gallagher . |
| 4,323,069 | 4/1982 | Ahr et al. ............................ 604/378 |
| 4,623,340 | 11/1986 | Luceri ................................. 604/378 |

FOREIGN PATENT DOCUMENTS

| | | | |
|---|---|---|---|
| 295912 | 5/1966 | Australia .............................. 604/372 |
| 0178108 | 4/1986 | European Pat. Off. ............ 604/372 |
| 0068367 | 5/1980 | Japan .................................... 604/372 |
| 2049553 | 12/1980 | United Kingdom . |
| 2055690 | 3/1981 | United Kingdom . |
| 2114895 | 9/1983 | United Kingdom . |

Primary Examiner—John E. Kittle
Assistant Examiner—Beth A. Bozzelli
Attorney, Agent, or Firm—Sughrue, Mion, Zinn, Macpeak & Seas

[57] ABSTRACT

A perforated covering structure is described for hygienic-sanitary products, such as sanitary towels for women, comprising an upper layer constituted by a non-woven textile of fibers of hydrophobic material, an intermediate layer or core constituted by a film of hydrophobic material, and a lower layer also constituted by a non-woven textile of fibers of hydrophobic material. The covering structure is applied in direct contact with that face of the absorbent core of the product which is intended to face the body of the user in use.

27 Claims, 3 Drawing Sheets

COVERING STRUCTURE FOR ABSORBENT HYGIENIC-SANITARY PRODUCTS, AND AN ABSORBENT PRODUCT HAVING SUCH A COVERING

FIELD OF THE INVENTION

The present invention relates in general to absorbent hygienic-sanitary products, such as sanitary towels for women, nappies or diapers for babies and incontinence pads for adults, swabs for surgery and tampons for medication, bandages, absorbent plasters, etc.

Such products, which are intended to absorb and retain body fluids such as menstrual fluids, urine, blood and exudetions, are used every day in the form of disposable products, that is, products intended to be thrown away after use. Because of their practicality and hygienic nature, they are in ever-more-widespread use and have practically superseded all those devices which are re-usable after washing, such as bandages, swaddling bands, etc., of conventional type.

The absorbent core of the product in constituted by a mat (ped or wad) of porous material which can absorb and retain a large quantity of fluid. The core can be divided into an "upper" face intended to face the body of the user and a "lower" face intended to face the external environment.

The absorbent core is covered by a covering sheet or structure generally having different characteristics on the upper and lower faces.

The covering sheet or structure applied to the upper face (topsheet), must in fact be permeable to body fluids so as to facilitate their flow into the absorbent core. On the other hand, the covering sheet or structure applied to the lower face (backsheet) must be impermeable to fluids so as to protect the clothing of the user, preventing it becoming wet.

The formation of an upper covering sheet or structure having optimum characteristics of use in one of the main problems to be solved in improving the qualities of absorbent products.

The upper covering sheet or structure must in fact fulfil various functions, often of an opposing nature.

In particular, it must allow easy penetration of the body fluids into the absorbent wad or core, while isolating the skin of the user from the absorbed fluids to avoid maceration of the skin itself.

It is very important then that the upper covering sheet or structure gives the user a feeling of superficial dryness even when the core of the product has absorbed a considerable quantity of fluid.

In the past, it has been proposed to use sheets of non-woven textile (that is, non-woven according to current English terminology) made from non-absorbent or hydrophobic fibres such as synthetic fibres for the upper covering structure. Thus, it is possible to prevent the user's skin from being exposed to prolonged contact with a wet coverng as occurs, however, when the absorbent product is covered with a woven textile or non-woven textile made from absorbent or hydrophylic fibres such as cotton, rayon, etc.

It has also been proposed to use for the upper covering an absorbent product constituted by a film of plastics material (itself impermeable to body fluids) rendered permeable by means of perforations of various shapes and sizes, with different distributions and densities depending on the requirements of use.

Such known covering structures, however, have disadvantageous side effects such as, in the case of non-woven, synthetic-fibre-based textiles, a residual tendency to retain and absorb the body fluids on the surface of the absorbent product, and, in the case of perforated plastics films, a disagreeable tactile sensation given to the user by the non-textile material.

OBJECT OF THE INVENTION

The object of the present invention is to provide a covering structure for hygienic-sanitary products, particularly for use as the covering structure for the upper face (as defined above) of such products, which has the following characteristics:
  an overall appearance and tactile sensation to the user substantially like the appearance and tactile sensation afforded by a textile product,
  the capacity to facilitate the penetration of body fluids into the absorbent core of the product, particularly with regard to menstrual fluids,
  a tendency of the upper surface of the product to keep itself substantially clean even when the core of the product has already absorbed a certain quantity of fluid,
  the possibility of preventing the fluid already absorbed by the core from being able to flow out of the product again, returning to the body of the user, and
  a capacity to isolate the moisture contained in the absorbent core.

SUMMARY OF THE INVENTION

According to the present invention, the object specified above is achieved by virtue of a covering structure for absorbent hygienic-sanitary products, characterised in that it is perforated and comprises:
  an upper layer intended to face outwardly of the absorbent product, constituted by a non-woven textile of fibres of hydrophobic material,
  an intermediate layer constituted by a film of hydrophobic material, and
  a lower layer intended to face inwardly of the absorbent product, constituted by a non-woven textile of fibres of hydrophobic material.

The present invention also provides an absorbent hygienic-sanitary product having an absorbent core with an upper face and a lower face, characterised in that it includes a covering structure of the type specified above applied in direct contact with the upper face.

DESCRIPTION OF THE INVENTION

Figure 2:
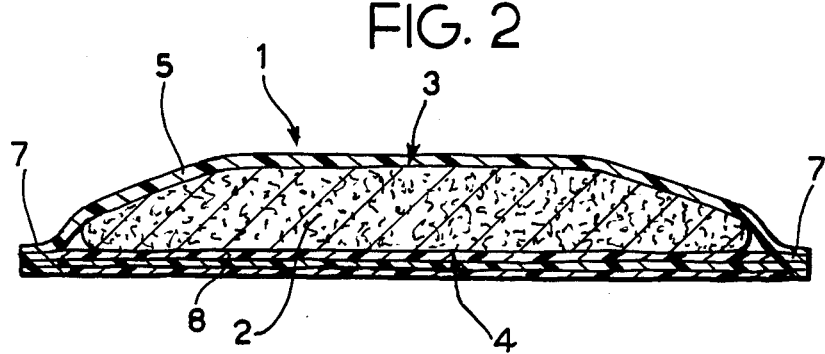
Figure 3:
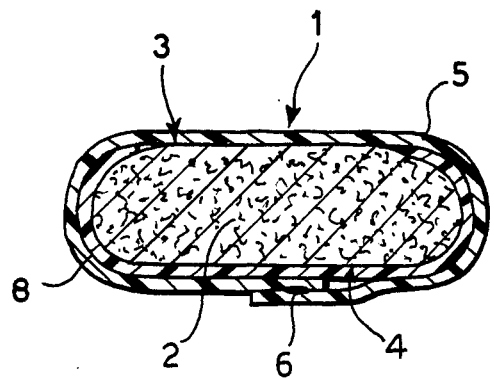
Figure 4:
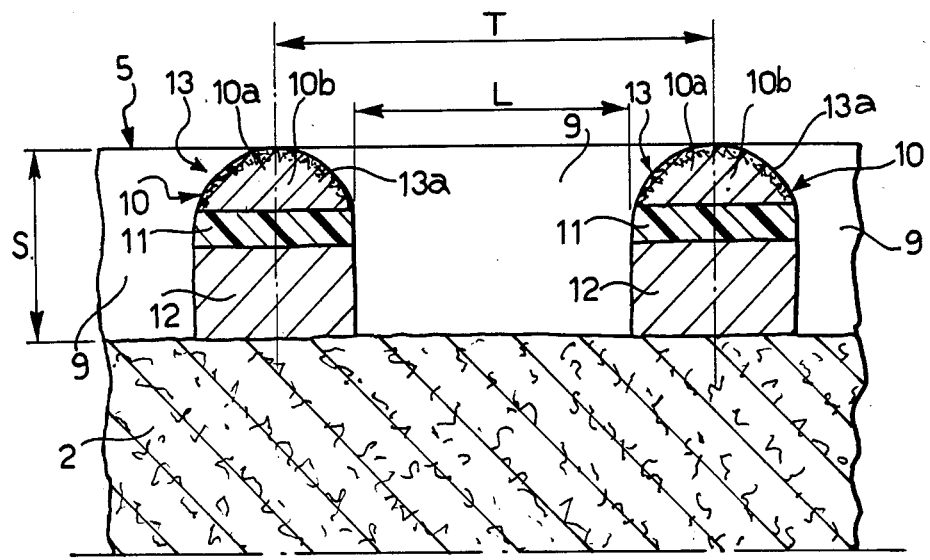
Figure 5:
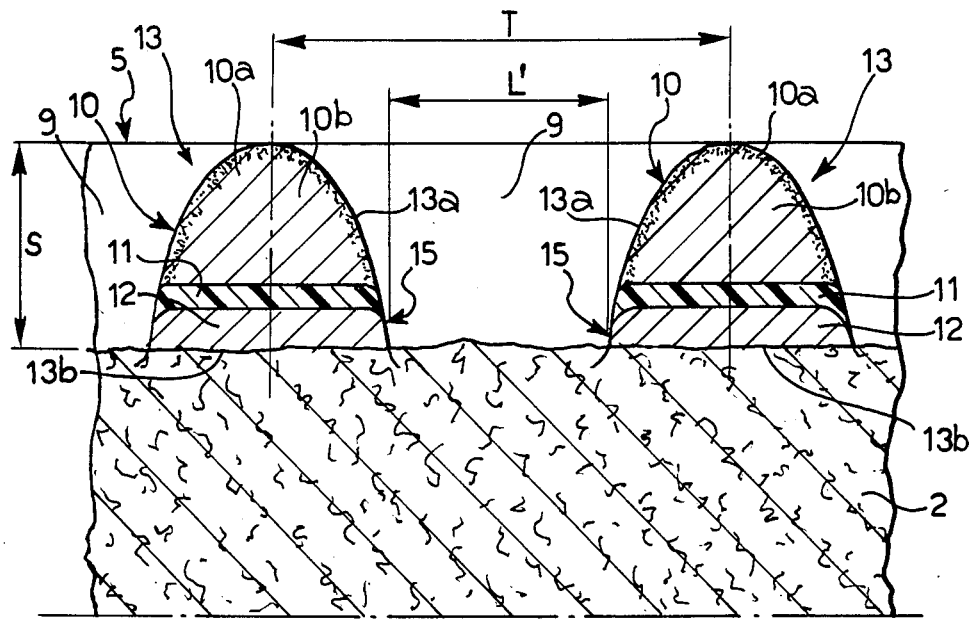
Figure 6:
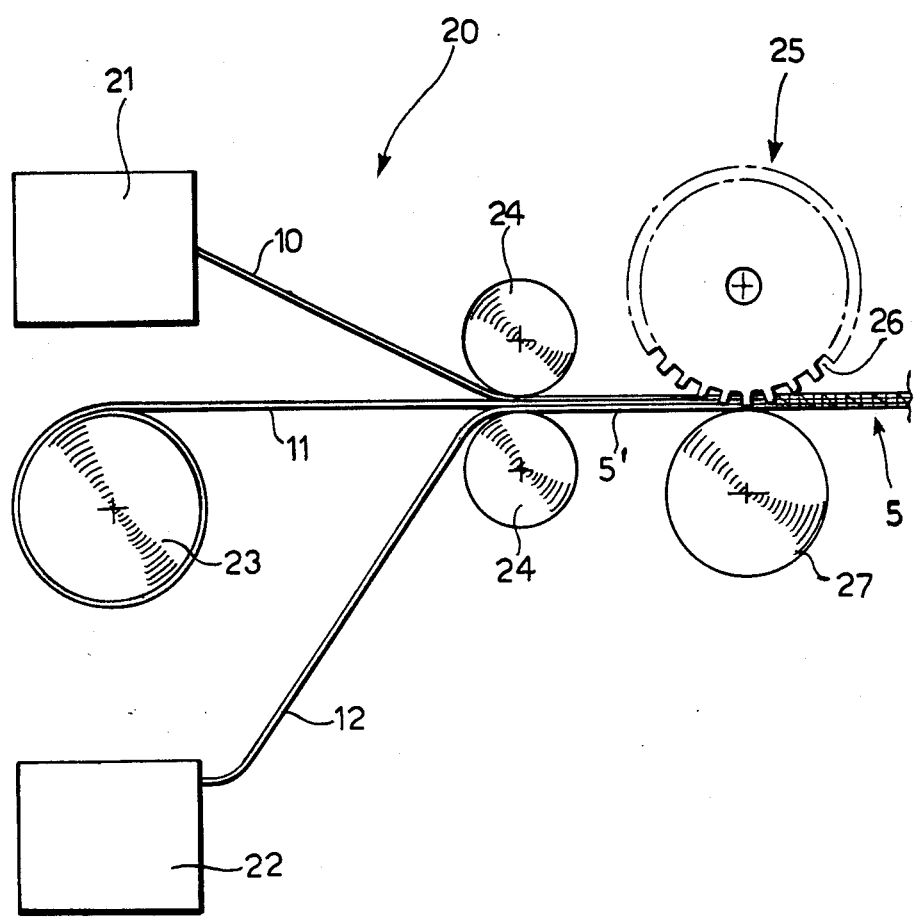

The present invention will now be described, purely by by way of non-limiting example, with reference to the appended drawings, in which:

FIG. 1 illustrates schematically an absorbent hygienic-sanitary product according to the invention, FIG. 2 is a section taken on the line II—II of FIG. 1, FIG. 3 is a section taken on the line III—III of FIG. 1, FIG. 4 is a sectional view, on an enlarged scale, of one of the elements of the absorbent product illustrated in FIGS. 1 to 3, FIG. 5 is a view substantially similar to the view of FIG. 4, illustrating a possible variant of the invention, and FIG. 6 illustrates schematically the method of manufacture of the elements illustrated in FIGS. 4 and 5.

The detailed description which follows is given with specific reference to a hygienic-sanitary product constituted by a sanitary towel for women.

The invention is not limited to this possible use, however, and may be applied to advantage to all absorbent hygienic-sanitary products and particularly to nappies or diapers for babies and incontinence pads for adults, surgical swabs and tampons for medication, bandages, absorbent plasters, etc.

In FIGS. 1 to 3 an absorbent product is generally indicated 1 and is constituted, as indicated above, by a sanitary towel for women.

The product 1 is constituted essentially by an absorbent mat or core 2 of generally elongate form in which an upper face 3 (intended to face towards the body of the user) and a lower face 4 (intended to face outwardly) can be distinguished.

The absorbent mat or core 2 is completely enveloped by a covering sheet or structure 5. The covering structure 5 is made from a strip which is closed into a tube, the opposite edges being superposed and connected together by strips of adhesive material 6 or by heat-sealing or ultrasonic welding.

The covering structure 5 is then also closed at the two ends of the mat 2 by heat-sealing or ultrasonic welding in the two end zones 7, which are generally arcuate and open towards each other. However, this operation may also be achieved, to advantage, by adhesives.

A sheet 8 of impermeable material is also interposed between the mat 2 and the covering structure 5 in correspondence with the lower face 4 and sides of the mat 2, in order to prevent the fluids absorbed by the mat 2 from being able to leave the pad itself and soil the user's clothes.

Naturally, it is also possible to make the outer covering of the mat 2 by using two different covering structures, of which that intended to be applied to the upper face 3 is perforated and has the layered structure which will be described more fully below, while the structure intended to be applied to the lower face 4 is, in general, an impermeable structure.

The description which follows is thus provided with specific reference to the upper covering structure of the product 1, that is, to the covering structure intended to be applied to the upper face 3 of the mat 2 in direct contact with the mat 2 itself.

The mat 2 is normally constituted - in known manner - by wood cellulose fibres treated pneumatically to form a highly porous material generally called airfelt or fluff. This material is preferred because of its low cost and its very good hydrophylic characteristics and good absorption of liquids.

The gram weight of the absorbent mat 2 may vary within wide limits according to the type of absorbent product (sanitary towel for women, disposable diapers, etc.) and, by way of example, may vary between 200 and 1200 g/m$^2$. The so-called "voluminosity" of the pad 2 may be chosen with the range 7 cc/g to 25 cc/g.

Naturally, lower voluminosities give rise to higher rates of diffusion of the fluids in the pad because of the lower value of the average radius of the capillaries which are formed between the cellulose fibres, while higher voluminosities give rise to greater overall absorption of fluid.

Even the nature and the method of manufacture of the cellulose fibres influences the processes of absorption and retention of fluids in the pad. Particularly preferred are coniferous wood cellulose fibres which are purified chemically, preferably without the addition of substances adapted to reduce the bonds between the fibres.

The best results have been obtained by the dry defibration of chemical cellulose sheets sold under the trade name "NBF FLUFF" by the Weyerhaeuser Corporation of Tacoma (U.S.A.).

As best seen in FIGS. 4 and 5, the covering structure 5 (which is applied in direct contact with the upper face of the mat 2) is perforated, holes 9 being provided and arranged in an ordered or pseudo-random array, and has a generally layered configuration.

This configuration can be seen to comprise essentially three layers, that is to say:
 an upper or outer layer 10 intended to face outwardly of the absorbent product 1, constituted by a non-woven textile of fibres of hydrophobic material,
 an intermediate layer or core 11 constituted by a film of hydrophobic material, and
 a lower or inner layer 12 intended to face the absorbent mat 2, constituted, like the upper layer 10, by a non-woven textile of fibres by hydrophobic material.

For the upper layer 10 which is intended to come into contact with the user's skin, the use of a non-woven textile of polypropylene fibres is preferred. This choice is preferred for the characteristics of safety, non-absorbency and cheapness of the fibres themselves.

The intermediate layer 11 is preferably constituted by a film of soft, white, low-density polyethylene film. It is also possible to use films of other types for the core layer, such as, for example, polypropylene films It is also considered preferable to use a non-woven textiles constituted by polypropylene fibres for the layer 12 which is disposed in direct contact with the absorbent mat 2. Naturally, synthetic fibres may be used for the upper and lower layers, for example, the two-component fibres CHISSO ES made by the Japanese company CHISSO.

The overall thickness of the covering structure, indicated S, may vary within a range of between 200 and 700 microns. This choice allows a good compromise to be achieved between the requirement of obtaining good penetration of the fluids into the mat 2 and the requirement of avoiding subsequent reflux of the fluids from the absorbent product 1. Furthermore, this choice gives good isolation of the wet content of the absorbent pad during use.

Particularly good results have been obtained with a thickness S in the range 250 to 550 microns. The currently preferred choice is a value of S of substantially 350 microns.

The overall basis weight of the covering structure 5, when a non-woven textile of polypropylene fibres is used for the outer layers 10 and 12 and a soft, white, low-density polyethylene film is used for the core layer 11, may vary within a range of from 20 to 60 g/m$^2$.

More particularly, the basis weight of individual layers may vary within the following ranges:
 7-40 g/m$^2$ for the upper layer 10,
 5-30 g/m$^2$ for the intermediate layer 11, and
 7-30 g/m$^2$ for the lower layer 12.

At present, the particularly preferred overall basis weight is 40 g/m$^2$, with values of 20 g/m$^2$ for the upper layer 10, 10 g/m$^2$ for the core layer 11, and 10 g/m$^2$ for the lower layer 12.

As indicated above, the holes 9 in the covering structure 5 may be arranged in a regular square, rectangular, rhomboidal or hexagonal array, or in a pseudo-random array.

The embodiment illustrated in FIG. 4 makes reference to square holes 9 the sides of which have a length L in FIG. 4 of about 0.7 mm. The embodiment of FIG. 5, however, relates to circular or slightly elliptical holes.

The interspacing between adjacent holes, corresponding to the distance T separating the median planes of the walls separating two adjacent holes, is about 1.4 mm.

Overall, the open area of the covering structure 5 (that is, the ratio between the surface occupied by the holes 9 and the whole surface of the structure) is about 25%.

Naturally, it is possible to use holes arranged in an array other than a sqaure array.

The choice of a square array of square holes (FIG. 4) or circular or slightly elliptical holes (FIG. 5) is considered preferable at present, however, since this choice enables the covering structure 5, and particularly the outwardly facing surface of the product 1, to be given an appearance substantially like the appearance of an ordinary woven textile, which is particularly pleasing to the user.

The diameters of the holes 9 may be different from those indicated above.

In general, for application to sanitary towels for women, the diameters of the holes 9 (this term being understood to mean the maximum dimension of the hole in the general plane of extension of the structure 5) is chosen in the range 0.4 to 1.5 mm, with a preferred choice of values within the range 0.6 to 0.9 mm.

The open area of the covering structure may be varied in dependence on the requirements of use and the strength characteristics of the materials use. It is typically within the range 10% to 50% with reference to the whole surface of the covering structure.

In general, as will be better seen below, the holes 9 are made by a perforating or punching action from the face of the covering structure intended to face outwardly of the product. Thus, the face 13a of the upper layer 10 of each wall or partition 13 of the structure 5 between two adjacent holes 9 which will face outwardly of the product can be made generally curved with its convexity facing outwardly of the structure 5, as is clearly shown in FIGS. 4 and 5.

This curved configuration facilitates the penetration of fluids into the holes 9 and consequently their absorption by the fibres of the absorbent pad 2. It thus tends to make the fluids slide into the holes 9, preventing the fluids from standing on the outer surface of the covering structure 5. This makes available a "cleaner" covering structure which does not tend to absorb the body fluids.

The formation of the holes 9 by perforation or punching also has the effect of causing a certain compaction of those fibres of the upper layer 10 which are closest to the outer surface of the layer itself.

In other words, in each of the separating walls or partitions 13, the upper layer 10 includes a surface portion 10a constituted by more compacted fibres and an inner portion 10b constituted by more loosely packed fibres.

The greater relative density of the outer portion 10a means that this portion is to a certain extent impermeable to the body fluids, or at least tends to absorb the body fluids to a lesser extent.

The softer and more absorbent inner portion 10b is thus completely protected from the exterior by the more compacted portion 10a on one side and by the film of hydrophobic material 11 on the other side.

During use, the absorption of the body fluids by the inner portion 10b is extremely low. It has also been possible to note that the density gradient of the material between the surface portion 10a and the inner portion 10b means that the latter absorbs practically no fluids from the exterior.

The outermost part of the covering structure 5 of the invention, that is, the part intended to come into direct contact with the user's skin, thus has a reduced tendency to absorb body fluids. This outer surface is thus virtually dry during use, which contributes to the user being given an agreeable feeling of cleanness.

The intermediate core layer 11, being constituted by a film of impermeable material, also acts as a barrier which prevents the fluids absorbed by the mat 2 from being able to migrate again towards the exterior of the product 1.

The most obvious difference between the covering structure illustrated in FIG. 4 and the variant of FIG. 5 lies in the fact that the outer surface of the layer 10 is more curved in the variant of FIG. 5, which enables better penetration of the body fluids into the absorbent mat 2. Another difference, already pointed out above, lies in the fact that the holes 9 are circular or slightly elliptical instead of square, with a diameter L' of the order of 0.8 mm. The upper layer 10 also has a greater thickness than that of the lower layer 12. An effect of partial covering of the lower region of each hole 9 by the intermediate film 11 is also apparent. This covering is caused by the fringes 15 of the film 11 which are formed during the formation of the holes 9 by perforation and which may even project towards the mat 2 beyond the surface of the covering structure.

In each case (FIG. 4 and FIG. 5), the lower layer 12 has the function of giving body to the covering structure 5, contributing to the isolation of the user from the fluids and moisture absorbed by the mat 2.

The surface of the lower layer 12 facing outwardly of the mat 2, the surface indicated 13b, is substantially flat.

This contributes to the keeping of the structure 5 in firm contact with the absorbent mat 2, particularly when the layers or spots of adhesive are applied between the surface 13b and the outer surface of the mat 2.

The close adhesion of the outer covering 5 to the absorbent mat 2 plays a considerable role in ensuring that the fluids which flow towards the surface 5 are not, so to speak, trapped within the holes 9 but are drawn into the mat 2.

This drawing effect on the fluids must be ensured not only immediately the product has been put on but even after prolonged use over a certain period of time, that is to say, after the product 1 has already been subject to the normal stresses of use.

It is thus very important to achieve substantially continuous and effective contact between the covering structure 5 and the mat 2. If account is taken of the nature of the mat 2, which is constituted by separate fibres that are not bound together, it is extremely advantageous to be able to provide flat surfaces, such as the surfaces 13b, which enable the use of adhesives to improve the connection between the covering structure 5 and the absorbent mat 2. For this purpose, glues in aqueous solution or heat-fusible glues, for example, applied lightly by known spreading methods, may be used to advantage.

More particularly, whenever glues in aqueous solution or suspension are used, the barrier function of the intermediate film 11 reduces the risk of the glue seeping towards the outer surface of the structure 5 and then coming into contact with the user's skin.

In the case of both cold glues in aqueous emulsion and heat-fusible glues, it is in fact usual to use rubber-based glues which keep their characteristics of stickiness and adhesiveness through pressure for a long time.

FIG. 6 shows schematically a device useable for manufacturing a covering structure such as that illustrated in FIGS. 4 and 5.

The device, generally indicated 20, comprises two cards 21, 22 each of which continuously supplies a web of polypropylene fibres.

The web supplied by the card 21 is intended to form the upper layer 10 and is thus indicated by this reference in FIG. 6.

Similarly, the web supplied by the card 22 is indicated 12 and is intended to constitute the lower layer 12 of the covering structure 5.

A film of low-density polyethylene, preferably milky-white in colour, intended to constitute the intermediate layer 11, is unwound continuously from a reel, generally indicated 23.

The webs 10 and 12 and the film 11 are fed towards two counter-rotating rollers 24 in a disposition such that the film 11 is interposed between the webs 10 and 12.

The rollers 24, the peripheral velocities of which are regulated so as to correspond to the velocity of supply of the webs 10 and 12 and the film 11, press the two webs 10 and 12 onto the two opposite faces of the film 11, joining the webs 10 and 12 and the film 11 into a single strip 5' having a layered structure.

One is thus dealing with a functional arrangement generally used in the manufacture of layered structures, such as, for example, covering sheets, floorings of the cushion floor type, etc. Naturally, in the present case, the pressure exerted by the rollers 24 must be regulated so as to avoid excessive squashing of the materials used.

The film 11 may then be connected to the webs 10 and 12 by means of adhesive or by the localised fusion of the film 11 achieved by heating of the rollers 24, etc.

The layered strip 5' is then directed to a perforating station, generally indicated 25, constituted by two counter-rotating superposed rollers 26, 27 with parallel axes.

The lower roller 27, which acts as a rotary support for the strip 5', has a generally smooth surface.

The upper roller 26, however, has teeth or projections arranged in an array correspondong to that of the holes 9 which it is wished to make in the strip 5.

The teeth or projections of the roller 26 penetrate the strip 5, giving the strip itself the perforated structure of the covering 5 and giving it form and strength.

The principle of operation of the unit 25 must be considered as generally known. The use of this solution for manufacturing the perforated structure 5 from the layered strip 5' has the double advantage of giving a generally curved form to the face 13a of the walls or partitions 13 separating the holes 9 and intended to face outwardly of the product, while also favouring the formation of the more compact zone 10a.

I claim:

1. A perforated, covering structure for absorbent hygienic-sanitary products comprising:
   an upper layer intended to face outwardly of the absorbent product, constituted by a non-woven textile of fibres of hydrophobic material,
   an intermediate layer constituted by a film of hydrophobic material, and
   a lower layer intended to face inwardly of the absorbent product, constituted by a non-woven textile of fibres of hydrophobic material;
   said structure having perforations separated by partitions defined, on the side intended to face outwardly of the absorbent product, by a curved face whose convexity faces outwardly of the structure.

2. A structure according to claim 1, wherein the upper layer is constituted by a non-woven textile of polypropylene fibres.

3. A structure according to claim 1 wherein the lower layer is constituted by a non-woven textile of polypropylene fibres.

4. A structure according to claim 1 wherein the intermediate layer is constituted by a film of material selected from polyethylene and polypropylene.

5. A structure according to claim 1 wherein the intermediate layer is constituted by a polyethylene film.

6. A structure according to claim 1, having an overall thickness of between substantially 200 and 700 microns.

7. A structure according to claim 1, having an overall thickness of between substantially 250 and 550 microns.

8. A structure according to claim 1, having an overall thickness of the order of 350 microns.

9. A structure according to claim 1, having an overall weight (basis weight) of between substantially 20 and 60 grams/m$^2$.

10. A structure according to claim 1 wherein the upper layer has a weight (basis weight) of between substantially 7 and 40 grams/m$^2$.

11. A structure according to claim 1 wherein the intermediate layer has a weight (basis weight) of between substantially 5 and 30 g/m$^2$.

12. A structure according to claim 1 wherein the lower layer has a weight (basis weight) of between substantially 7 and 30 g/m$^2$.

13. A structure according to claim 1, having a weight (basis weight) of the order of 40 g/m$^2$.

14. A structure according to to claim 1, wherein the upper layer has a weight (gram weight) of the order of 20 g/m$^2$, the intermediate layer has a weight (basis weight) of the order of 10 g/m$^2$, and the lower layer has a weight (basis weight) of the order of 10 g/m$^2$.

15. A structure according to claim 1, having an open area of between substantially 10 and 50%.

16. A structure according to claim 1, having an open area of the order of 25%.

17. A structure according to claim 1, having perforations with diameters of between substantially 0.4 and 1.5 mm.

18. A structure according to claim 1, having perforations with diameters of between substantially 0.6 and 0.9 mm.

19. A structure according to claim 1, having perforations of a square section with sides having a length of the order of 0.7 mm, spaced from each other by a distance of the order of 1.4 mm.

20. A structure according to claim 1, having perforations of circular or slightly elliptical section.

21. A structure according to claim 1 wherein the said upper layer has a surface portion which is relatively compact and an inner portion which is relatively soft.

22. A structure according to claim 21 wherein in each of the partitions the inner portion is completely isolated from the exterior by the surface portion and by the film of hydrophobic material.

23. A structure according to claim 1 having perforations separated by partitions defined, on the side intended to face inwardly of the absorbent product. by a substantially flat face.

24. An absorbent hygienic-sanitary product having an absorbent core with an upper face and a lower face, including a perforated covering structure which comprises:
- an upper layer intended to face outwardly of the absorbent product, constituted by a non-woven textile of fibres of hydrophobic material,
- an intermediate layer constituted by a film of hydrophobic material, and
- a lower layer intended to face inwardly of the absorbent product, constituted by a non-woven textile of fibres of hydrophobic material;

said structure having perforations separated by partitions defined, on the side intended to face outwardly of the absorbent product, by a curved face whose convexity faces outwardly of the structure.

25. A hygienic-sanitary product according to claim 24, wherein the intermediate layer adjacent said perforations is provided with fringes which extend towards the absorbent core.

26. A hygienic-sanitary product according to claim 24, wherein the absorbent core is constituted by a mat of fibres of hydrophylic material having a weight (basis weight) of between substantially 200 and 1200 g/m$^2$.

27. A hygienic-sanitary product according to claim 24, wherein the absorbent core is constituted by cellulose fibres.

* * * * *